US00PP17949P2

(12) United States Plant Patent
van der Knaap

(10) Patent No.: US PP17,949 P2
(45) Date of Patent: Aug. 28, 2007

(54) ***KALANCHOE* PLANT NAMED 'DON FREDERICO'**

(50) Latin Name: *Kalanchoe blossfeldiana*
Varietal Denomination: Don Frederico

(75) Inventor: Leonardus Johannus Maria van der Knaap, Naaldwijk (NL)

(73) Assignee: Knaap Licenties B.V., Naaldwijk (NL)

( * ) Notice: Subject to any disclaimer, the term of this patent is extended or adjusted under 35 U.S.C. 154(b) by 84 days.

(21) Appl. No.: 11/259,309

(22) Filed: Oct. 26, 2005

(51) Int. Cl.
*A01H 5/00* (2006.01)

(52) U.S. Cl. ..... Plt./338

(58) Field of Classification Search ..... Plt./335, Plt./338

See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Kalanchoe* plant named 'Don Frederico', characterized by its upright and freely branching plant habit; dark green-colored leaves; yellow-colored double flowers with multiple petals per flower; and excellent postproduction longevity.

1 Drawing Sheet

Botanical designation: *Kalanchoe blossfeldiana.*
Cultivar denomination: 'Don Frederico'.

BACKGROUND OF THE INVENTION

The present invention relates to a new and distinct cultivar of *Kalanchoe* plant, botanically known as *Kalanchoe blossfeldiana,* and hereinafter referred to by the name 'Don Frederico'.

The new *Kalanchoe* is a product of a planned breeding program conducted by the Inventor in Naaldwijk, The Netherlands. The objective of the breeding program was to create new freely-flowering *Kalanchoe* cultivars with multiple flower petals, attractive flower coloration and excellent postproduction longevity.

The new *Kalanchoe* originated from a cross-pollination made in Naaldwijk, The Netherlands on Jun. 30, 2003, of a proprietary selection of *Kalanchoe blossfeldiana* identified as code number 2000033, not patented, as the female, or seed, parent with a proprietary selection of *Kalanchoe blossfeldiana* identified as code number 20000335-1, not patented, as the male, or pollen, parent. The new *Kalanchoe* was discovered and selected by the Inventor as a single flowering plant within the progeny of the stated cross-pollination grown in a controlled environment in Naaldwijk, The Netherlands on Jul. 5, 2004.

Asexual reproduction of the new *Kalanchoe* by terminal cuttings at Naaldwijk, The Netherlands, has shown that the unique features of this new *Kalanchoe* are stable and reproduced true to type in successive generations.

BRIEF SUMMARY OF THE INVENTION

The cultivar Don Frederico has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Don Frederico'. These characteristics in combination distinguish 'Don Frederico' as a new and distinct cultivar:

1. Upright and freely branching plant habit.
2. Dark green-colored leaves.
3. Yellow-colored double flowers with multiple petals per flower.
4. Excellent postproduction longevity.

Plants of the new *Kalanchoe* differ primarily from plants of the female parent selection primarily in flower color as plants of the female parent selection have purple-colored flowers.

Plants of the new *Kalanchoe* differ primarily from plants of the male parent selection in leaf color as plants of the male parent selection have darker green-colored leaves.

Plants of the new *Kalanchoe* can be compared to plants of the *Kalanchoe* cultivar Don Garcia, disclosed in a U.S. Plant Patent application Ser. No. 11/259,308. In side-by-side comparisons conducted in Naaldwijk, The Netherlands, plants of the new *Kalanchoe* differed from plants of the cultivar Don Garcia in the following characteristics:

1. Leaves of the plants of the new *Kalanchoe* had acute apices and bases whereas leaves of plants of the cultivar Don Garcia had rounded apices and bases.
2. Plants of the new *Kalanchoe* had yellow-colored flowers whereas plants of the cultivar Don Garcia had pink-colored flowers.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe.*

The photograph at the top of the sheet comprises a side perspective view of a typical flowering potted plant of 'Don Frederico'.

The photograph at the bottom of the sheet comprises a close-up view of a typical flowering plant of 'Don Frederico'.

DETAILED BOTANICAL DESCRIPTION

In the following description, color references are made to The Royal Horticultural Society Colour Chart, 2001 Edition, except where general terms of ordinary dictionary significance are used. Plants used in the photographs and for the following observations and measurements were grown in Naaldwijk, The Netherlands, under commercial practice in a glass-covered greenhouse for about 14 weeks after planting with day temperatures ranging from 20° C. to 30° C., night temperatures ranging from 18° C. to 25° C. and light levels ranging from 5 to 60 kilolux. Plants used in the description and photographs were not pinched.

Botanical classification: *Kalanchoe blossfeldiana* cultivar Don Frederico.

Parentage:

*Female, or seed, parent.*—Proprietary selection of *Kalanchoe blossfeldiana* identified as code number 2000033, not patented.

*Male, or pollen, parent.*—Proprietary selection of *Kalanchoe blossfeldiana* identified as code number 20000335-1, not patented.

Propagation:

*Type cutting.*—Terminal cuttings.

*Time to initiate roots, summer.*—About ten days at 21° C.

*Time to initiate roots, winter.*—About 14 days at 21° C.

*Time to produce a rooted young plant, summer.*—About three weeks at 21° C.

*Time to produce a rooted young plant, winter.*—About four weeks at 21° C.

*Root description.*—Fine, fibrous; white in color.

*Rooting habit.*—Freely branching.

Plant description:

*Form/growth habit.*—Upright and rounded plant habit; freely flowering habit with numerous compound cymes. Actual plant shape will depend on whether or not plants are pinched (terminal apices removed). Vigorous growth habit.

*Branching habit.*—About twelve lateral branches per plant. Pinching is not required but will enhance lateral branch development.

*Plant height at flowering.*—About 20 cm.

*Plant diameter at flowering.*—About 30 cm.

*Lateral branch description.*—Length: About 10 cm to 13 cm. Diameter: About 5 mm. Internode length: About 5 mm. Strength: Strong. Texture: Smooth, glabrous. Color: 146B.

*Foliage description.*—Arrangement: Opposite, simple. Length: About 4 cm to 13 cm. Width: About 2.5 cm to 11 cm. Shape: Ovate. Apex: Broadly acute. Base: Acute. Margin: Crenate. Texture, upper and lower surfaces: Smooth, glabrous; leathery; succulent. Venation pattern: Pinnate; reticulate. Color: Developing foliage, upper surface: 137A. Developing foliage, lower surface: 147B. Fully expanded foliage, upper surface: Close to 147A; venation, 137C. Fully expanded foliage, lower surface: 147B; venation, 146B. Petiole length: About 1 cm to 2 cm. Petiole diameter: About 5 mm. Petiole texture, upper and lower surfaces: Smooth, glabrous. Petiole color, upper surface: 137C. Petiole color, lower surface: 146B.

Flower description:

*Flower type and habit.*—Double flowers with multiple petals arranged in compound dichasial cymes that arise from leaf axils. Freely flowering habit. Flowers persistent.

*Natural flowering season.*—Flowering year-round when flower initiation and development is induced under short day/long night conditions.

*Time to flower.*—About ten weeks with short day/long night conditions are required to produce flowering plants. Time to flower is primarily dependent upon temperature and light intensity.

*Post-production longevity.*—Plants of the new *Kalanchoe* maintain good leaf and flower substance for about four to six weeks under interior environmental conditions.

*Cyme height.*—About 5 cm.

*Cyme diameter.*—About 6 cm to 7 cm.

*Flowering habit.*—Freely flowering, potentially about 144 flowers per plant.

*Flower buds.*—Shape: Ovoid. Length: About 8 mm. Width: About 3 mm. Color: 150D.

*Flower diameter.*—About 1.5 cm.

*Flower depth (height).*—About 1 cm.

*Petals.*—Quantity: About 15 per flower. Length: About 9 mm. Width: About 4 mm. Shape: Spatulate. Apex: Apiculate. Base: Fused. Margin: Entire. Texture, upper and lower surfaces: Glabrous, smooth. Color: When opening, upper surface: 12A. When opening, lower surface: 12C. Fully opened, upper surface: 13C; color becoming closer to 11A with development. Fully opened, lower surface: 12C; color becoming closer 12D with development.

*Sepals.*—Quantity: About four per flower. Length: About 6 mm. Width: About 1 mm. Shape: Lanceolate. Apex: Acute. Base: Fused. Margin: Entire. Texture, upper and lower surfaces: Glabrous, smooth. Color: When opening and fully opened, upper and surface: 144A. When opening and fully opened, lower surface: 144A.

*Peduncles.*—Length: About 7 cm. Diameter: About 2 mm to 4 mm. Angle: Erect to about 45° from vertical. Strength: Moderately strong. Texture: Smooth, glabrous. Color: 146B.

*Pedicels.*—Length: About 5 mm. Diameter: About 1 mm. Angle: Erect to about 45° from vertical. Strength: Moderately strong. Texture: Smooth, glabrous. Color: 146B.

*Reproductive organs.*—Stamens: Stamen number: About four per flower. Anther length: About 1 mm. Anther shape: Oval. Anther color: 11A. Pollen amount: None observed. Pistils: Pistil number: About four per flower. Pistil length: About 7 mm. Style length: About 2 mm. Style color: 145B. Stigma shape: Round. Stigma color: 151C. Ovaries: Superior and four-celled. Ovary color: 145B.

*Seeds.*—Seed development has not been observed.

Disease/pest resistance: Resistance to known pathogens and pests common to *Kalanchoe* has not been observed on plants of the new *Kalanchoe* grown under commercial greenhouse conditions.

Temperature tolerance: Plants of the new *Kalanchoe* have been observed to tolerate temperatures from 5° C. to 35° C.

It is claimed:

1. A new and distinct cultivar of *Kalanchoe* plant named 'Don Frederico', as illustrated and described.

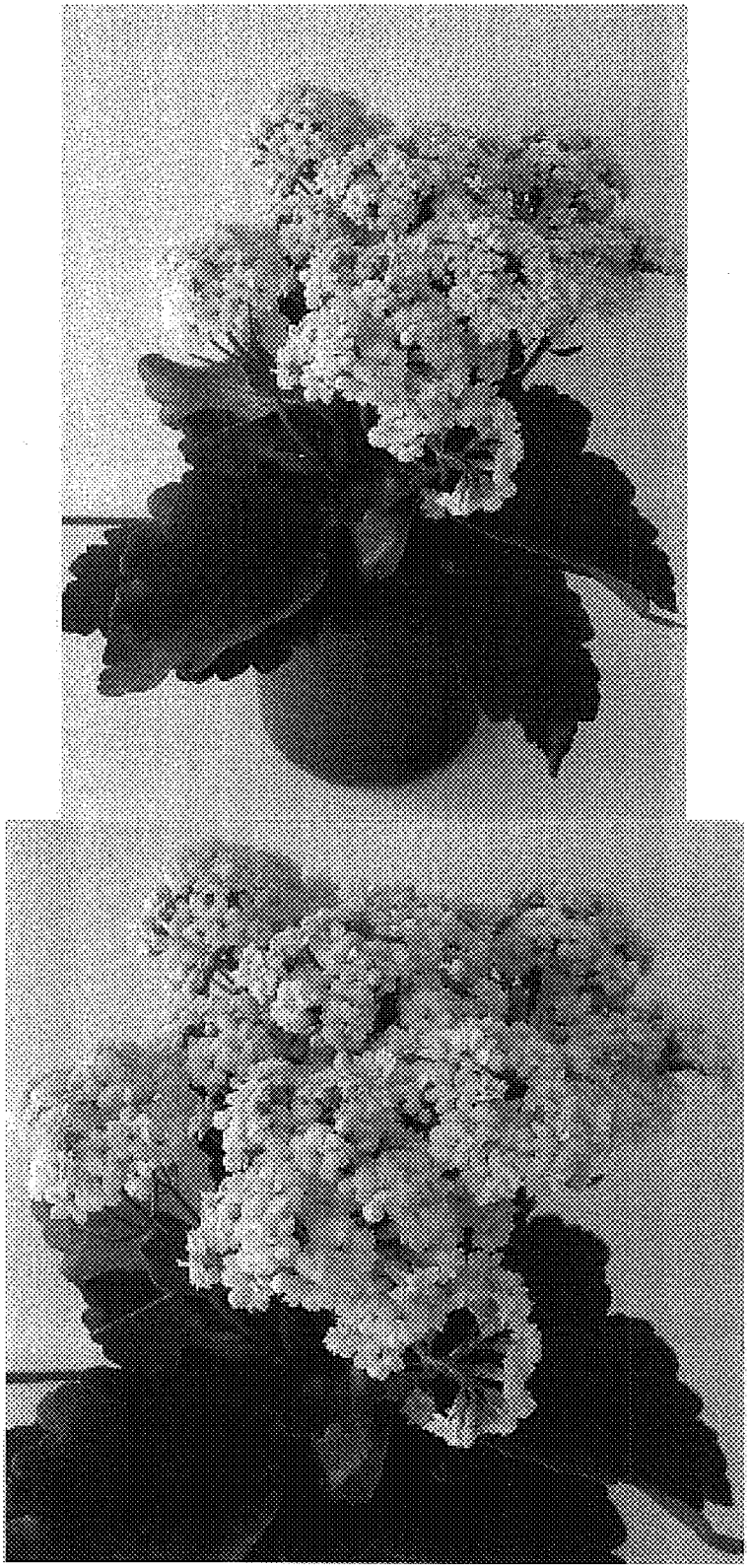

* * * * *